United States Patent [19]

Jaffe

[11] Patent Number: 5,622,182
[45] Date of Patent: Apr. 22, 1997

[54] SYSTEM FOR MEASURING CORE BODY TEMPERATURE IN VIVO

[76] Inventor: Richard A. Jaffe, 786 Wildwood La., Palo Alto, Calif. 94303

[21] Appl. No.: 266,252

[22] Filed: Jun. 27, 1994

[51] Int. Cl.⁶ .................................................... A61B 5/00
[52] U.S. Cl. ............................................ 128/736; 128/633
[58] Field of Search ................................ 128/633, 634, 128/734, 736, 660.01, 660.02, 716, 719

[56] References Cited

U.S. PATENT DOCUMENTS

| | | |
|---|---|---|
| 3,998,550 | 12/1976 | Konishi et al. . |
| 4,170,997 | 10/1979 | Pinnow et al. . |
| 4,176,660 | 12/1979 | Mylrea et al. . |
| 4,223,680 | 9/1980 | Jöbsis . |
| 4,248,217 | 2/1981 | Brisson . |
| 4,281,645 | 8/1981 | Jöbsis . |
| 4,305,388 | 12/1981 | Brisson . |
| 4,337,761 | 7/1982 | Upsher . |
| 4,383,534 | 5/1983 | Peters . |
| 4,444,185 | 4/1984 | Shugar . |
| 4,453,552 | 6/1984 | Ensign . |
| 4,537,190 | 8/1985 | Caillot et al. . |
| 4,565,194 | 1/1986 | Weerda et al. . |
| 4,567,882 | 2/1986 | Heller . |
| 4,584,998 | 4/1986 | McGrail . |
| 4,648,396 | 3/1987 | Raemer . |
| 4,691,701 | 9/1987 | Williams . |
| 4,728,499 | 3/1988 | Fehder . |
| 4,730,622 | 3/1988 | Cohen . |
| 4,738,266 | 4/1988 | Thatcher . |
| 4,742,819 | 5/1988 | George . |
| 4,750,495 | 6/1988 | Moore et al. . |
| 4,800,886 | 1/1989 | Nestor . |
| 4,809,706 | 3/1989 | Watson et al. . |
| 4,819,752 | 4/1989 | Zelin . |
| 4,859,057 | 8/1989 | Taylor et al. . |
| 4,903,701 | 2/1990 | Moore et al. . |
| 4,907,594 | 3/1990 | Muz . |
| 5,005,573 | 4/1991 | Buchanan . |
| 5,069,222 | 12/1991 | McDonald, Jr. . |
| 5,163,755 | 11/1992 | Shimomura et al. . |
| 5,193,544 | 3/1993 | Jaffe . |

*Primary Examiner*—Sam Rimell
*Attorney, Agent, or Firm*—Majestic, Parsons, Siebert & Hsue

[57] ABSTRACT

A system and method of using same is provided for deriving accurate measurements of core body temperature of a subject. A temperature sensing device is provided for sensing a temperature-related parameter of the subject and generating a first signal representative thereof, and a respiratory gas sensing device is provided for sensing a respiration-related parameter of the subject and generating a second signal representative thereof. Additionally, signal correlation device connected to the temperature and respiration sensing devices is provided for determining from the second signal an optimal time interval for measuring the core body temperature of the subject and obtaining from the first signal a value for core body temperature during that interval.

17 Claims, 6 Drawing Sheets

SYSTEM FOR MEASURING CORE BODY TEMPERATURE IN VIVO

INCORPORATION BY REFERENCE OF RELATED PATENT

Incorporated herein by this reference is the entire disclosure of U.S. Pat. No. 5,193,544 to Richard A. Jaffe which issued on Mar. 16, 1993 from application Ser. No. 650,824 which was filed on Jan. 31, 1991.

BACKGROUND OF THE INVENTION

This invention relates to a system and a method for measuring the core body temperature of a patient. More particularly, the present invention relates to a system and a method for deriving the core body temperature from measurements of respired gas temperature.

The measurement of body temperature during surgery and in other critical care situations is essential for the appropriate clinical management of any patient. Hypothermia during general anesthesia is a common occurrence especially in pediatric and elderly patient populations which can be associated with undesirable consequences including reduced drug metabolism and excretion, hemodynamic instability and delayed awakening. During the recovery period following general anesthesia, the hypothermic patient must attempt to restore normal body temperature, commonly through shivering thermogenesis and peripheral vasoconstriction to conserve heat. However, shivering can increase the body's oxygen consumption by up to 500 percent, leading to the possibility of decreasing the oxygen available to the heart and brain. Additionally, vasoconstriction decreases peripheral blood flow which may interfere with the normal healing process. In view of complications such as these, it is often desirable to measure and to monitor the core body temperature of a patient.

The most accurate sites for measuring core temperature include the pulmonary artery, the tympanic membrane, the distal esophagus and the nasopharynx. However, not all of these sites are ideal. Access to the pulmonary artery site requires pulmonary artery catheterization, an invasive procedure that is usually not performed for temperature monitoring alone. Temperature measurement at the tympanic membrane requires very careful probe placement and risks damage to the tympanic membrane. The esophageal site is safe, but the temperature probe must be carefully positioned to avoid cooling by inspired gases in the adjacent trachea. Nasopharyngeal temperature measurements are very prone to error as a result of movement of the temperature probe and cooling effects of respired gases.

A measurement site within the trachea would be most convenient, since nearly every patient undergoing general anesthesia has an endotracheal tube placed in the trachea to protect the airway and to enable breathing (or ventilation) during anesthesia. Unfortunately, systems and methodologies for measuring temperature within the trachea provide inaccurate temperature measurements as the result of cooling by inspired gases.

SUMMARY OF THE INVENTION

A principal object of the present invention is to provide a system and a method for deriving accurate measurements of core body temperature of a patient or subject from a site within a subject's trachea or an endotracheal tube inserted into a subject's trachea.

The present invention is based on the observation that measurement of the core body temperature of a subject at or near a tracheal site is most accurate when that temperature is sensed during the expiratory portion of the subject's respiratory cycle, when perturbating inspired gases are absent from the tracheal lumen. Particularly, such a temperature measurement is most accurate when temperature sensing takes place during an optimal time interval corresponding to an end-tidal portion of the respiratory cycle. Thus, by sensing a parameter related to a subject's respiratory cycle, determining therefrom the end-tidal portion of the respiratory cycle and the corresponding optimal time interval, and correlating the optimal time interval with the sensing of a temperature-related parameter, one can obtain an accurate value for the core body temperature of a subject.

The core body temperature measuring system of the present invention includes any of a variety of temperature sensing devices which is capable of sensing a temperature-related parameter of a subject, such as voltage, resistance, color change, infrared emission, optical transmission, or the like, and generating a first signal representative of that parameter. The system also includes any of a variety of respiratory gas sensing devices which is capable of sensing a respiration-related parameter such as carbon dioxide or oxygen concentration, thoracic impedance, the direction of respiratory flow, or the like, and generating a second signal representative of that parameter. Connected to the temperature sensing and respiratory gas sensing devices is a signal correlation device which correlates the first and second signals. From the second signal, the signal correlation device determines an optimal time interval for measuring the patient's core body temperature. From the first signal, the signal correlation means obtains a value for the core body temperature of the subject during the optimal time interval.

The core body temperature measurement method of the present invention includes sensing a temperature-related parameter of a subject and generating a first signal representative of the temperature-related parameter; sensing a respiration-related parameter of respired gases of the subject and generating a second signal representative of the respiration-related parameter; and determining from the second signal an optimal time interval for measurement of a core body temperature of the subject and obtaining from the first signal a value for the core body temperature during the optimal time interval.

DETAILED DESCRIPTION OF THE INVENTION

In this description, reference numbers used to reference items described herein with respect to one of FIGS. 1A–4D are the same reference numbers used to describe similar items described with respect to any of the remaining FIGS. 1A–4D, unless otherwise noted.

Figure 1A:
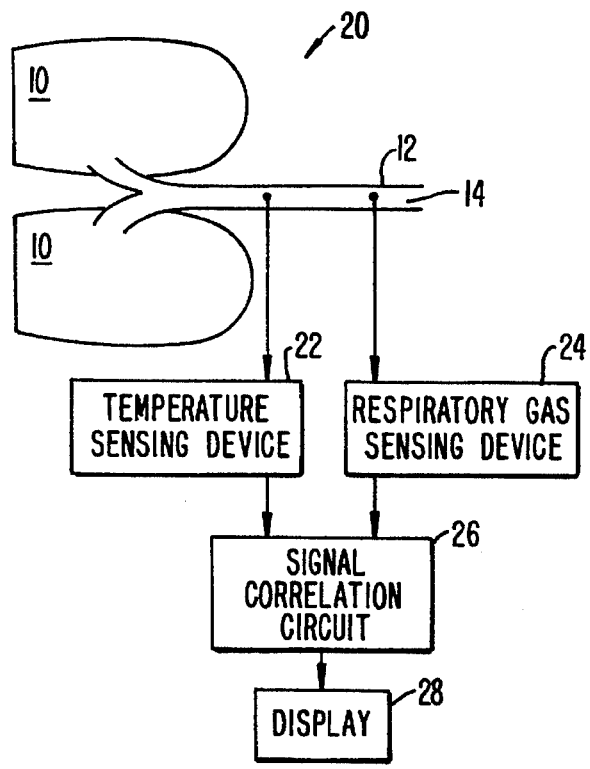
FIG. 1A is a schematic illustration of a system for enabling the measurement of core body temperature in vivo, according to an embodiment of the present invention. The system includes a temperature sensing device, a respiratory gas sensing device, and signal correlation means.

FIG. 1A is a schematic illustration of a system for enabling the measurement of core body temperature in vivo, according to an embodiment of the present invention. FIG. 1A shows the lungs 10, the trachea 12, and the tracheal lumen 14 of a subject. System 20 of FIG. 1A includes a temperature sensing device 22, a respiratory gas sensing device 24, signal correlation device or circuit 26, and a receiver display 28.

Temperature sensing device 22 of system 20 is used to sense a temperature-related parameter of the subject and to generate a first signal representative of the temperature-related parameter. Temperature sensing device 22 may be designed to sense a variety of alternative temperature-related parameters, the most typical being voltage, resistance, color change, infrared emission and optical transmission. By way of example, temperature sensing device 22 may include a thermocouple or a thermistor for sensing voltage or resistance, a temperature-sensitive dye or a temperature-sensitive liquid crystal display for sensing color change, an infrared sensor for sensing infrared emission, or an optical or infrared sensor for sensing optical transmission. As a particular example of the use of infrared sensing, temperature sensing device 22 includes an infrared sensor positioned in the tracheal lumen 14 or the breathing pathway of the subject to sense infrared emission from the respired gases of the subject. According to another aspect of the present invention, further described herein in relation to FIG. 4B, temperature sensing device 22 includes an optical path which is coupled to a sensor for sensing the temperature-related parameter and may further include an optical fiber.

Temperature sensing device 22 preferably provides a first signal with a fast response time (such as a time constant of less than one second and preferably, about 0.1 second or less). Thus, the first signal generated by temperature sensing device 22 easily follows fairly rapid temperature changes.

Respiratory gas sensing device 24 of system 20 is used to sense a respiration-related parameter of the subject and to generate a second signal representative of the respiration-related parameter. Respiratory gas sensing device 24 may be designed to sense a variety of alternative respiration-related parameters, the most typical being an analyzer for measuring carbon dioxide or oxygen concentration of gases respired by the subject. By way of example, such analyzers include infrared analyzers for measuring infrared absorption of the respired gases, mass spectrometers, and analyzers which are adapted to Raman scattering techniques such as the adapted clinical gas monitor "Rascal" by Ohmeda of Englewood, Colo.

Figure 1B:
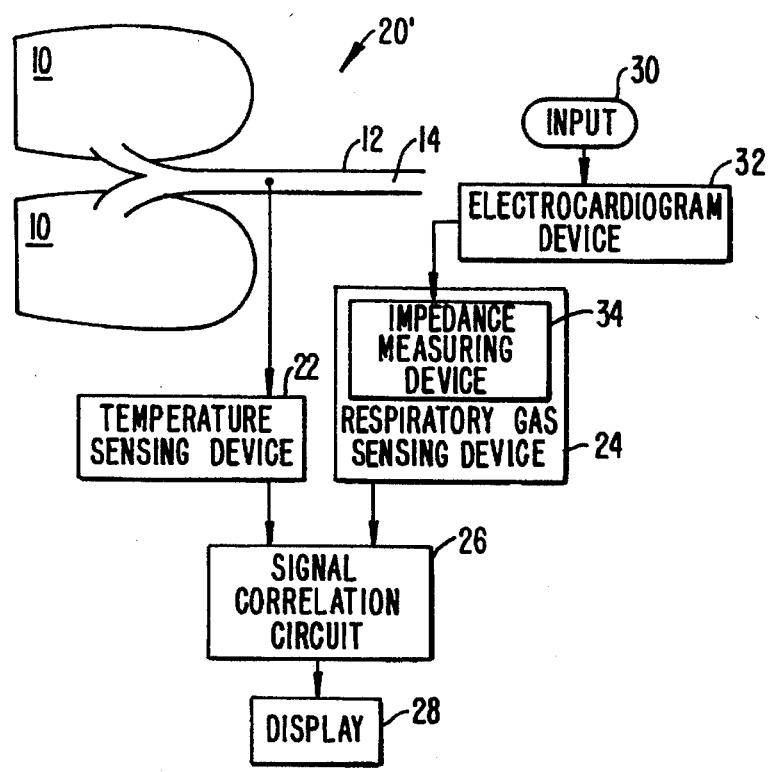
FIG. 1B is a schematic illustration of such a system according to another embodiment of the present invention.

According to an alternative embodiment, schematically illustrated in FIG. 1B, respiratory gas sensing device 24 includes an impedance measuring device 34, which is in electrical communication with an electrocardiograph (ECG) device 32 (i.e., via ECG leads), for measuring thoracic impedance. In such an embodiment, ECG device 32 receives electrical input 30 from the thoracic cavity of the subject and generates a signal which is representative of either electrical currents transversing the heart of the subject or electrical potentials associated therewith. The ECG signal is then communicated to the impedance measuring device 34 of respiratory sensing device 24 for measuring thoracic impedance.

Figure 1C:
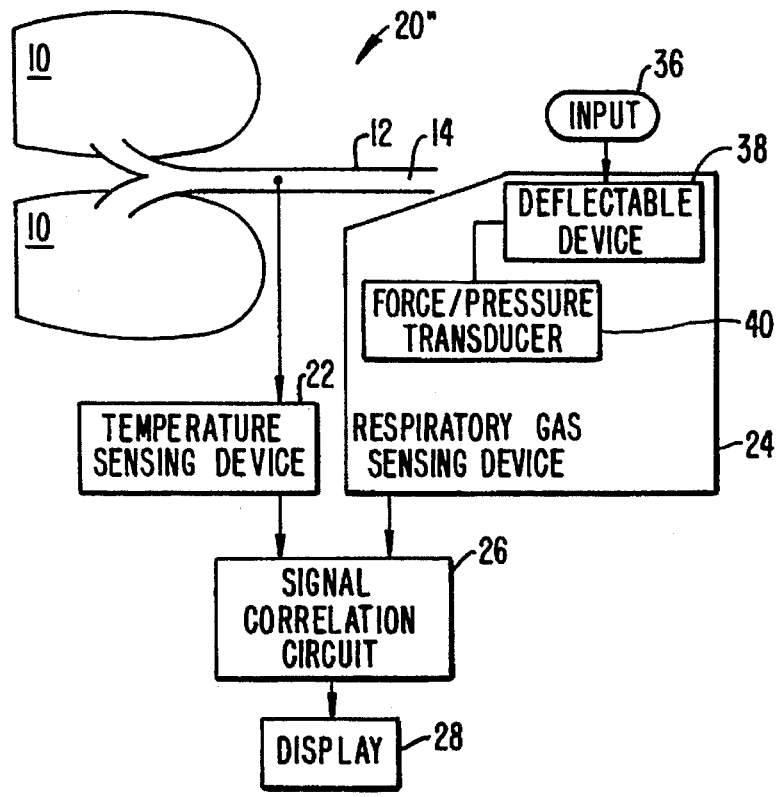
FIG. 1C is a schematic illustration of such a system according to another embodiment of the present invention.

According to another alternative embodiment, schematically illustrated in FIG. 1C, respiratory gas sensing device 24 is adapted to sense a direction of a flow of gases respired by the subject. Such a respiratory sensing device 24, further described herein in relation to FIG. 4C, includes a deflectable device 38 that is capable of being substantially deflected by the force or pressure of the flow of respired gases, designated as input 36. Connected to deflectable device 38 is a force or pressure transducer 40, which is responsive to a deflection of device 38 by input 36. In use, the deflectable device 38 is deflected in substantially one direction during inspiration, or inhalation, of respired gases and in substantially an opposite direction during expiration, or exhalation, of respired gases. Upon such directional deflection of device 38, force or pressure transducer 40 generates a signal representative of the flow direction of respired gases.

Figure 2:
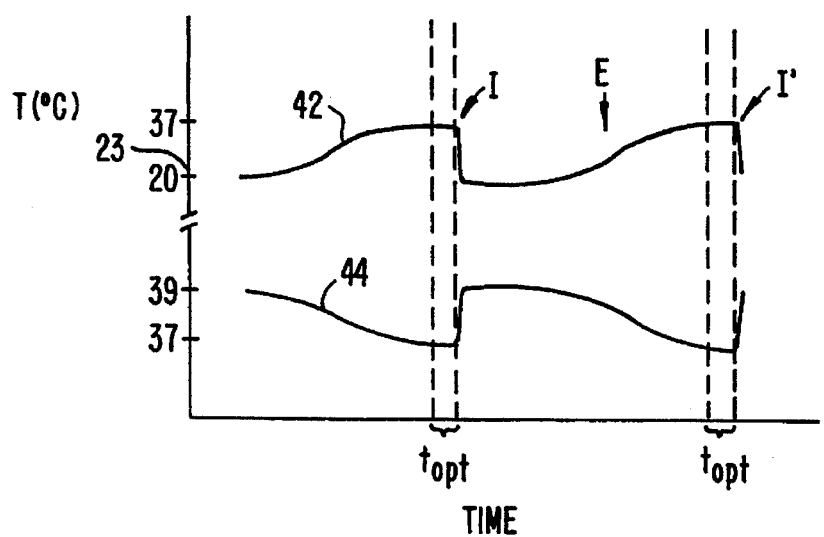
FIG. 2 is a graphic illustration of temperature versus time during respiration.

FIG. 2 is a graphic illustration of temperature versus time during respiration of gases by a subject. When temperature sensing device 22 of FIGS. 1A–1C is located within trachea 12 or tracheal lumen 14, temperature sensing device 22 generates a signal 42, as shown in FIG. 2, that is substantially representative of the temperature of inspired gases, at about room temperature, alternating with the temperature of respired gases which have equilibrated with the core body temperature of the subject as a result of heat transfer in the alveoli of lungs 10. FIG. 2 illustrates signal 42, starting with an inspiration gas temperature of from about 20 degrees Centigrade (room temperature) to about 23 degrees Centigrade, progressing in time to an expiration gas temperature shown as about 37 degrees Centigrade, further progressing in time to a sharp decrease in respired gas temperature from the expiration gas temperature to an new inspiration gas temperature upon a new respiratory inspiration I, and repeating a similar signal later in time for a new respiratory cycle from this new respiratory inspiration I through respiratory expiration E to yet another respiratory inspiration I'.

FIG. 2 also illustrates an alternative signal 44 which is similarly generated by temperature sensing device 22. However, in this case, temperature sensing device 22 is sensing the temperature of respired gases when the inspired gases are warmer than the expired gases, such as when the subject is being warmed by external means. Thus, signal 44 of FIG. 2 starts at a preheated inspiration gas temperature shown as about 39 degrees Centigrade, progressing in time to an expiration gas temperature shown as about 37 degrees Centigrade, further progressing in time to a sharp increase in respired gas temperature from the inspiration gas temperature to a new inspiration gas temperature upon a new respiratory inspiration I, and repeating a similar signal later in time for a new respiratory cycle from this new respiratory inspiration I through respiratory expiration E to yet another respiratory inspiration I' of warmed gases.

In the present invention, it is desirable to measure the temperature of the subject during an optimal time interval, $t_{opt}$, such that it represents the core body temperature of the subject. The optimal time interval for measuring the temperature of the subject is shown in FIG. 2 by the two $t_{opt}$ designations, one for each of the two respiratory cycles shown, which correspond to the two sets of vertical dashed lines, respectively, intersecting signals 42 and 44. As shown in FIG. 2, the optimal time interval corresponds to an expiratory portion of the respiratory cycle, when the respired gas temperature is most likely to match the true core body temperature of the subject. Determination of the optimal time interval is further described herein in relation to FIG. 3.

Figure 3:
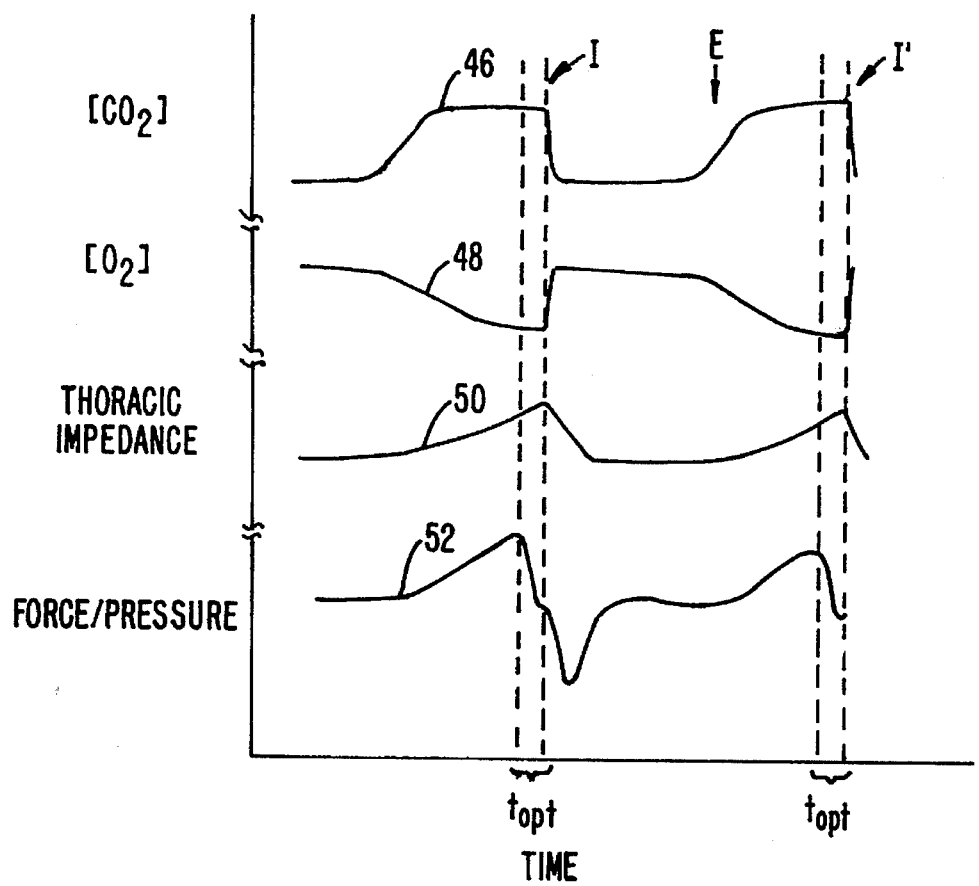
FIG. 3 is a graphic illustration of carbon dioxide concentration ($[CO_2]$), oxygen concentration ($[O_2]$), thoracic impedance, and force or pressure versus time during respiration.

FIG. 3 is a graphic illustration of carbon dioxide concentration ($[CO_2]$), oxygen concentration ($[O_2]$), thoracic impedance, and force or pressure versus time during respiration of gases by a subject. When respiratory gas sensing device 24 of FIGS. 1A–1C is located within trachea 12 or tracheal lumen 14, respiratory gas sensing device 24 generates a signal 46, 48, 50, or 52 as shown in FIG. 3, that is substantially representative of a respiration-related parameter of carbon dioxide concentration, oxygen concentration, thoracic impedance, or force or pressure, respectively.

Particularly, FIG. 3 illustrates carbon dioxide concentration signal 46, starting with a low inspiration $[CO_2]$, progressing in time to an increased expiration $[CO_2]$, further progressing in time to sharp decrease in respiratory $[CO_2]$ from a new respiratory inspiration I, and repeating a similar signal later in time for a new respiratory cycle from new respiratory inspiration I through respiratory expiration E to yet another respiratory inspiration I'. In the present invention, carbon dioxide concentration signal 46 is particularly preferred as an indicator of an end-tidal portion of the respiratory cycle which is further described below in relation to the optimal time interval. FIG. 3 also illustrates alternative oxygen concentration signal 48, starting with a high inspiration $[O_2]$, progressing in time to a decreased expiration $[O_2]$, further progressing in time to sharp increase in respiratory $[O_2]$ from a new respiratory inspiration I, and repeating a similar signal later in time for a new respiratory cycle from new respiratory inspiration I through respiratory expiration E to yet another respiratory inspiration I'.

Similarly, FIG. 3 illustrates the progress of alternative thoracic impedance signal 50 and alternative force or pressure signal 52 from inspiration to expiration and repeating later in time over a new respiratory cycle from new inspiration I through expiration E to yet another new inspiration I'. Thoracic impedance signal 50 of FIG. 3 represents a substantially rhythmic parameter related to the respiratory cycle. Signal 52 of FIG. 3 particularly shows the change in respiratory flow direction from new inspiration I (deflection in one direction) through expiration E (deflection in an opposite direction) in the optimal time interval, $t_{opt}$, preceding subsequent inspiration I'.

In FIG. 3, the optimal time interval is shown by the two $t_{opt}$ designations, one for each of the two respiratory cycles shown, which correspond to the two sets of vertical dashed lines, respectively, intersecting the respiration-related signals 46 through 52. As explained above in relation to FIG. 2, the optimal time interval for measuring core body temperature corresponds to an expiratory portion of the respiratory cycle, when the respired gas temperature is most likely to match the true core body temperature of the subject. The expiration of respired gases occurs over a period which includes an end-tidal respiratory interval. Preferably, the optimal time interval substantially corresponds to the end-tidal respiratory interval. Most preferably, this end-tidal respiratory interval is obtained from carbon dioxide concentration signal 46 of FIG. 3.

Signal correlation device 26 of FIGS. 1A–1C is used to correlate the signal generated by temperature sensing device 22 ("first signal") with the signal generated by respiratory gas sensing device 24 ("second signal") to obtain a value for the core body temperature of the subject during the optimal time interval. In particular, signal correlation device 26 is connected to temperature sensing device 22 and respiratory sensing device 24. From the second signal, which represents a respiration-related parameter, signal correlation device 26 determines an optimal time interval for measurement of a core body temperature of the subject. Preferably, the optimal time interval substantially corresponds to the end-tidal respiratory interval. From the first signal, which represents a temperature-related parameter, signal correlation device 26 obtains a value for the core body temperature of the subject during the optimal time interval.

Figure 5:
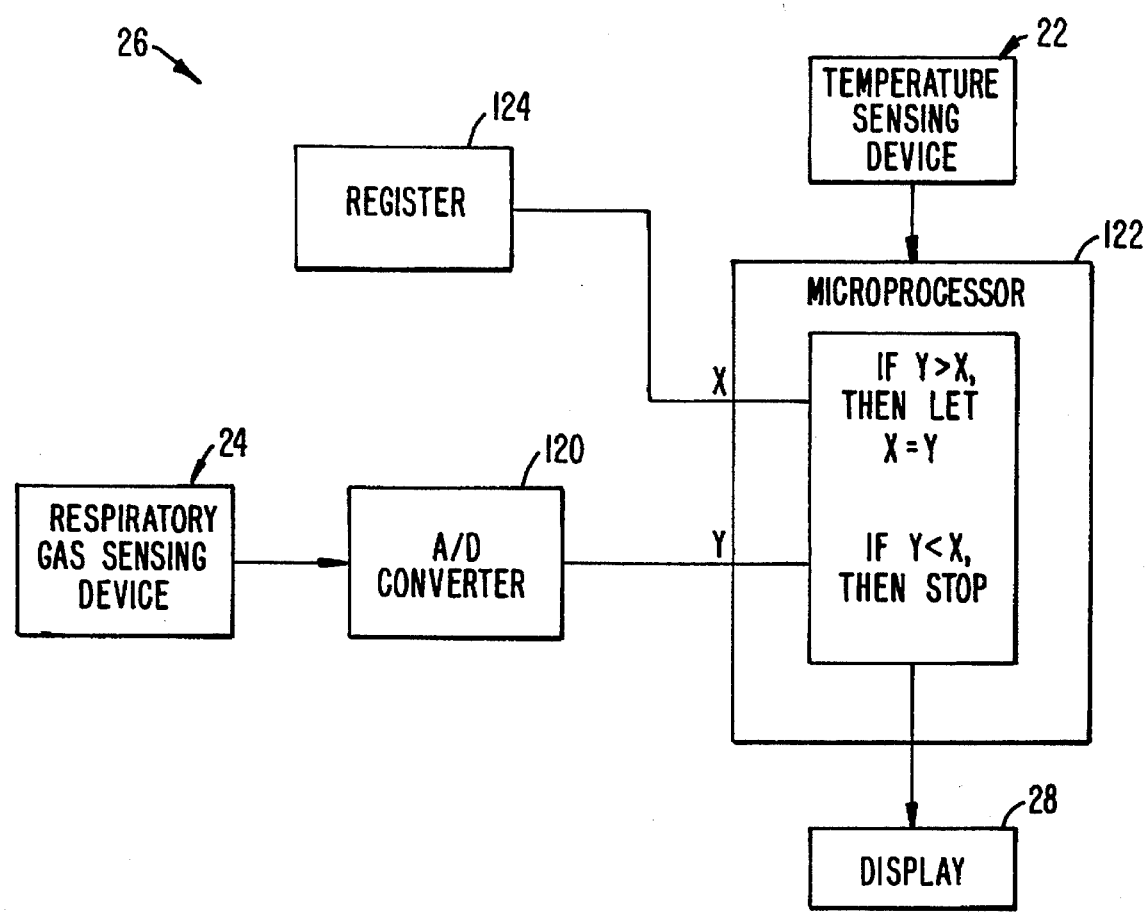
FIG. 5 is a schematic block diagram of the signal correlation device shown in FIGS. 1A–1C.

Signal correlation device 26 is now described in relation to the schematic block diagram of FIG. 5. Particularly, signal correlation device 26 receives the second signal from the respiratory gas sensing device 24. Upon reaching an analog-to-digital (A/D) converter of the signal correlation device 26, the second signal is digitized to obtain a representative digital value Y for subsequent processing. Value Y is then processed in a microprocessor 122 of the signal correlation device 26.

An initial low value is first stored in register 124 as X. Microprocessor 122 then compares the values X and Y. When a maximum value for the second signal is sought to determine the peak of the second signal, the initial value stored as X is chosen so that it is less than any digitized value of the second signal likely to be encountered. Therefore, microprocessor 122 will find that the value Y is greater than the value X. In such event, microprocessor 122 will replace the value X stored in register 124 with the output value Y of converter 120. Thus, output value Y becomes the new value stored in register 124 as X. Upon the next sampling of the output of converter 122 by microprocessor 122, a new digitized value Y of the second signal will be obtained and compared to the value of X in register 124. If the value of Y is greater than the value X then stored in register 124, again the value Y will be stored as the new value of X in register 124. This sampling and comparison process by microprocessor 122 will continue until it finds that a sample Y is found to be less than the stored value X, at which point the maximum value X for or peak of the second signal has been reached. The time interval during which the peak of the second signal occurs is then determined by the microprocessor 122. In this manner, the signal correlation circuit 26 determines the optimum time interval during which the peak of the second signal, such as the peak of $[CO_2]$ signal 46 or thoracic impedance signal 50 of FIG. 3, occurs.

While the operation of the signal correlation device 26 in FIG. 5 is illustrated above to determine the maximum or peak of a second signal, it is understood that the above-described operation of device 26 would need to be modified only slightly for determining the minimum or bottom of the valley of the second signal, such as $[O_2]$ signal 48 of FIG. 3. To this end, the above-described operation of device 26 is modified in the following manner. The initial value stored as X in register 124 is chosen so that it is expected to be larger than the digitized value of the second signal at all times. The output value Y of converter 120 is sampled and compared with value X stored in register 124. If the microprocessor finds that the value Y is smaller than the value X, then the value Y replaces value X in register 124 and becomes the new value stored in register 124 as X. This sampling and comparison process is repeated by microprocessor 122 until it finds a sample Y which is greater than the value X stored in the register. The microprocessor then determines the time period during which the sampling of such value X occurs, which defines the optimum time interval for determining core body temperature. It is understood that in order to determine an inflection or transition in the second signal, such as the force/pressure signal 52 of FIG. 3, the above-described operation of device 26 again needs to be modified in terms of the comparison criteria to define the optimum time period during which such inflection and transition occurs.

However the optimal time interval is determined, it is used as the basis for determining of the core body temperature of the subject from the first signal from the temperature sensing device 22. Particularly, the microprocessor 122 of the signal correlation device 26 also receives the first signal from the temperature sensing device 22. Once the optimal time interval corresponding to the maximum, minimum, or inflection of the second signal is determined, microprocessor 122 finds the value of the first signal in the optimal time interval to determine the value of the temperature-related parameter corresponding to that optimal time interval. Signal correlation device 26 then converts the value of the temperature-related parameter to temperature to obtain a value for the core body temperature of the subject. This temperature value is then relayed to display 28 where the core body temperature of the subject is displayed.

While signal correlation device 26 may be adapted to obtain one value for the core body temperature of the subject for each respiratory cycle, it may alternatively or additionally include a circuit for calculating an average of the core body temperature value over at least one respiratory cycle. The systems 20, 20' and 20" of FIGS. 1A, 1B and 1C, respectively, may further include a receiver display 28, which is connected to signal correlation device 26 and adapted to display either a core body temperature value, an average core body temperature, or both. Preferably, the display circuit 28 displays the core body temperature value, average, or both, continuously until the next optimal time interval and/or averaging period is reached whereupon the display is updated to reflect the value and/or average corresponding to the new optimal time interval and/or averaging period.

In a preferred embodiment, the temperature-related parameter and the respiration-related parameter are simultaneously sensed by temperature sensing device 22 and respiratory gas sensing device 24, respectively, and the first signal and the second signal generated respectively thereby are correlated via signal correlation device 26 to determine an optimum time interval for temperature measurement. Preferably, signal correlation device 26 of FIGS. 1A–1C obtains a value for the core body temperature of a subject during the optimal time interval substantially corresponding to an end-tidal interval as determined by carbon dioxide concentration signal 46 of FIG. 3.

A simpler approach involves recording all of the sampled values of the second signal and the sampling times associated therewith to find the time periods during which the peak, valley or transition of the second signal occurs.

In systems 20, 20' and 20" of FIGS. 1A–1C, temperature sensing device 22 need not be located in the trachea 12 or the tracheal lumen 14, although such locations are preferred. Alternative sites in the respiratory gas stream of a subject for temperature sensing device 22 include sites adjacent a wall of an endotracheal tube, preferably at a distal end thereof which is closest to the lungs 10; adjacent a connector to an endotracheal tube which is connected to a proximal end thereof (farthest from the lungs 10); or adjacent an attachment to the proximal endotracheal tube connector. If the latter two sites are chosen, the temperature sensing device 22 of system 20 may include means for sensing external temperature and means for compensating for a reduction in temperature at the external sensing site. Typically, empirical calibration is used for such compensation.

Figure 4A:
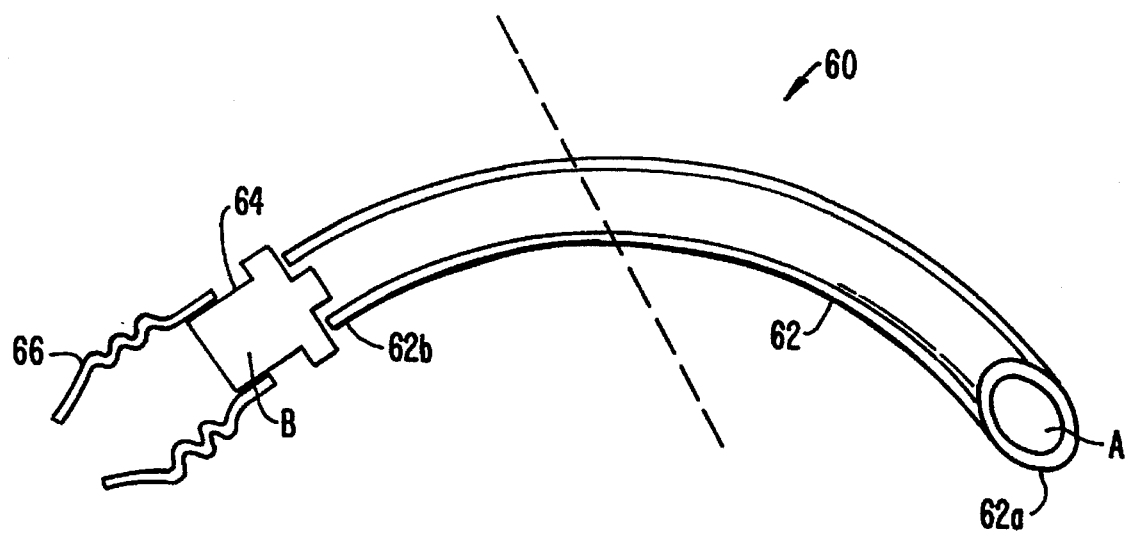
FIG. 4A is a longitudinal cross-sectional view of an endotracheal tube to illustrate an embodiment of the present invention.
Figure 4B:
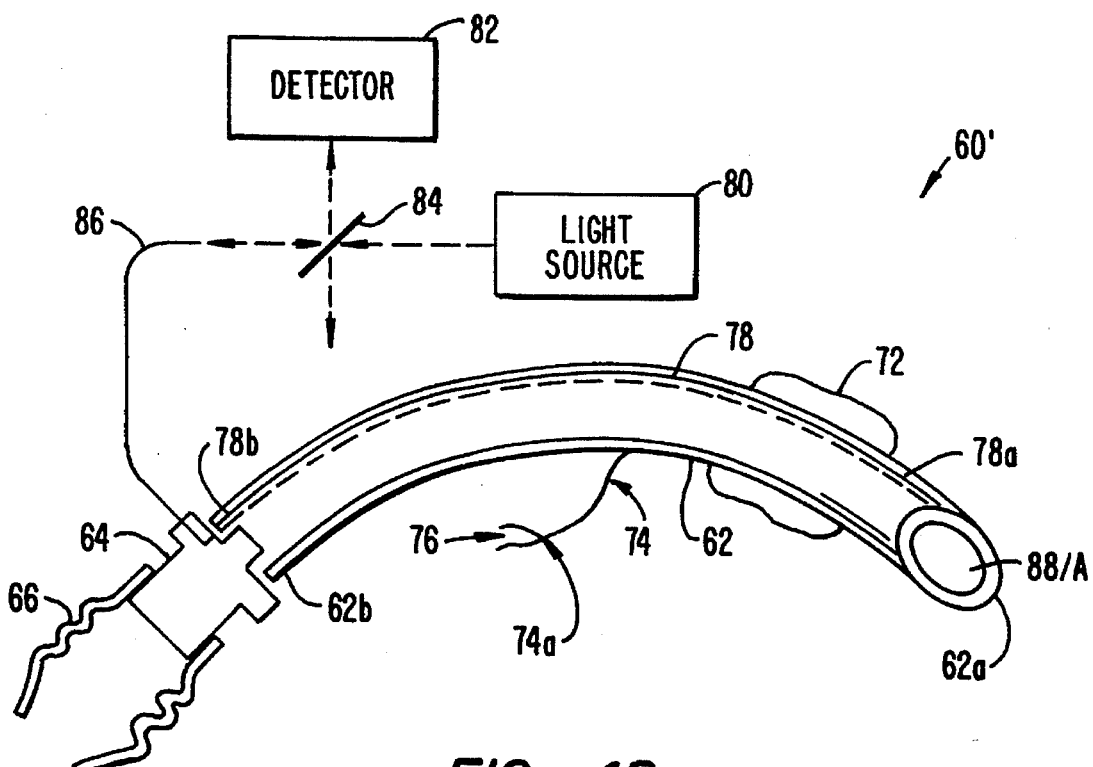
FIG. 4B is a longitudinal cross-sectional view of an endotracheal tube including an optical path to illustrate another embodiment of the present invention.

FIGS. 4A and 4B provide a longitudinal cross-sectional view of endotracheal tube systems 60 and 60', respectively, for conveying gases to and from a subject's trachea 12 of FIGS. 1A–1C and for measuring physiological parameters in vivo, according to various embodiments of the present invention. System 60 of FIG. 4A includes an endotracheal tube 62 and a connector 64 connecting tube 62 to another tube 66 of a respirator (not shown). Distal end 62a of tube 62 is suitable to be inserted into the trachea of a human or animal subject and proximal end 62b is adapted to be connected to connector 64. Oxygen or air is then supplied through tube 66, connector 64 and tube 62 to the trachea of the subject and respired gases are allowed to escape through tube 62, connector 64 and tube 66 in the reverse direction in order to assist respiration of the subject. In such manner, system 60 forms a part of the medical support equipment for assisting the respiration of the subject during medical procedures, such as when the subject is anesthetized.

Distal end 62a, being the end of the tube which is inserted into the subject, is referred to below as the subject end. The angled dashed line in FIG. 4A divides tube 62 into two portions, the portion including subject end 62a being disposed substantially within the subject and the portion including proximal end 62b being disposed substantially external to the subject. Cuff 72, shown in FIG. 4B, is an inflatable sleeve near the subject end of tube 62. Cuff 72 provides a leak-resistant fit between the tube and the trachea 12 of FIGS. 1A–1C to prevent aspiration of stomach contents, saliva and blood through the tube and allows positive pressure to be applied to the lungs 10 of FIGS. 1A–1C. The cuff also serves to center the tube in the trachea. In order to inflate cuff 72, a small inflating tube 74 with an input end 74a is attached to the wall or lumen of tube 62 and a small passage within the wall or lumen is provided between tube 74 and cuff 72. In such manner, cuff 72 may be inflated by injecting a gas or liquid along direction 76 to the free end 74a of the inflating tube after end 62a has been inserted into the trachea of the subject and tube 62 is in place in the trachea. The function of tube 62 described above up to this point is essentially the same as that of conventional endotracheal tubes.

Figure 4C:
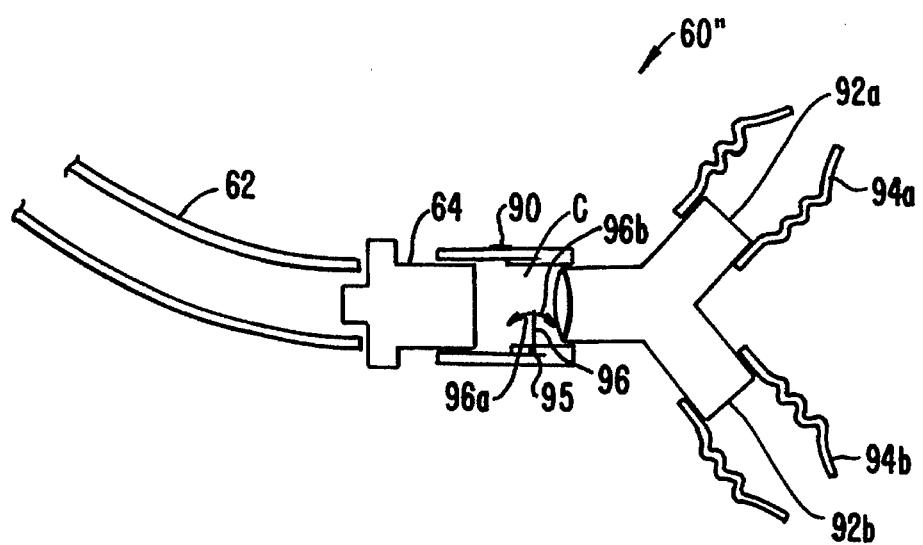
FIG. 4C is a longitudinal cross-sectional view of an endotracheal tube including an adapter and a connector to illustrate yet another embodiment of the present invention.

Temperature sensing device 22 of FIGS. 1A–1C may be disposed along endotracheal tube 62, either along the wall of tube 62 or as part of tube 62. Preferably, temperature sensing device 22 is disposed deep within tracheal lumen 14 of FIGS. 1A–1C or endotracheal tube 62 positioned within the tracheal lumen. In FIG. 4A, such location is shown generally as site A, adjacent distal end 62a of tube 62. Alternatively, temperature sensing device 22 may be located along endotracheal tube 62 from distal end 62a to proximal end 62b, adjacent proximal end 62b, or along connector section 64. The latter site is shown generally as site B, adjacent connector 64, the intermediate sites lying along endotracheal tube 62 between sites A and B. Additionally, as shown in the embodiment of FIG. 4C, temperature sensing device 22 may be disposed even further from the subject at a site C adjacent an attachment to connector 64. As described above, when measuring sites external to the subject (on the proximal side of the dashed line of FIG. 4A) are chosen, empirical calibration may be used to improve the accuracy of the temperature measurement.

FIG. 4B is a longitudinal cross-sectional view of endotracheal tube 62 including an optical path 78 to illustrate another embodiment of the present invention. As shown in FIG. 4B, the wall or lumen of tube 62 includes an optical path 78 with a first end 78a and a second end 78b. End 78b is connected to a light source 80 and a detector 82 through a beam splitter 84 and to optical path 86, where optical path 86 is optically connected to end 78b through connector 64 at one end and to beam splitter 84 at the other end.

According to this embodiment, temperature sensing device 22 includes an optical path 78 and a sensor 88 for sensing a temperature-related parameter which is optically coupled to optical path 78. While the sensor 88 may be located at any of the abovedescribed sites, it is shown generally at site A in FIG. 4B. In use, light source 80 provides light in the infrared spectral region to optical path 86 through beam splitter 84. The light provided travels through path 86 and path 78. When such light reaches end 78a of path 78, the light transverses sensor 88 where it undergoes a change of intensity as a function of the temperature of the sensor. Accordingly, the intensity of the transmitted light is diminished as the temperature of temperature sensor 88 is increased. After transversing the sensor, light is reflected therefrom such that it travels in the reverse direction towards end 78b and path 86 and is directed by beam splitter 84 towards detector 82. The detector 82 detects the intensity of the reflected light in the infrared region in order to determine the temperature of temperature sensor 88 and thus, the body temperature of the subject at the site of the sensor.

In system 60' of FIG. 4B, temperature sensor 88 is preferably an optical or an infrared sensor. Preferably, temperature sensor 88 is located and site A. In a preferred embodiment, optical path 78 forms part of endotracheal tube 62 and includes at least one optical fiber which is embedded in tube 62.

As with temperature sensing device 22 of system 60, respiratory gas sensing device 24 of FIGS. 1A–1C may be located at any of the previously discussed sites, although site A of FIGS. 1A and 1B is preferred. An alternative site C is described below in relation to the embodiment of FIG. 4C, in which respiratory gas sensing device 24 is adapted to sense a direction of a flow of respired gases.

FIG. 4C is a longitudinal cross-sectional view of an endotracheal tube 62, shown in part, including an adapter 90 and a connector 92 to illustrate yet another embodiment of the present invention. Adaptor 90 is attached at one end to endotracheal tube connector 64, opposite the connection of connector 64 and endotracheal tube 62, and at the other end to connector 92. In FIG. 4C, connector 92 is shown as a "Y" connector branching towards an end 92a and another end 92b. Ends 92a and 92b are connected, respectively, to respirator tubes 94a and 94b which lead, respectively, to and from a respirator (not shown).

Positioned within adapter 90 is a force or pressure transducer 95 which is connected to a substantially deflectable vane 96. In operation, deflectable vane 96 is responsive to a direction of the flow of respired gases, being deflected in the direction of arrow 96a upon inspiration and in the direction of arrow 96b upon expiration. In turn, force or pressure transducer 95 is responsive to the force or pressure caused by the directional deflection of vane 96 during respiration. Thus, when respiratory gas sensing device 24 including such a deflectable vane and transducer adapter 90 is employed, a respiratory-related second signal 52 of FIG. 3 is generated.

Figure 4D:
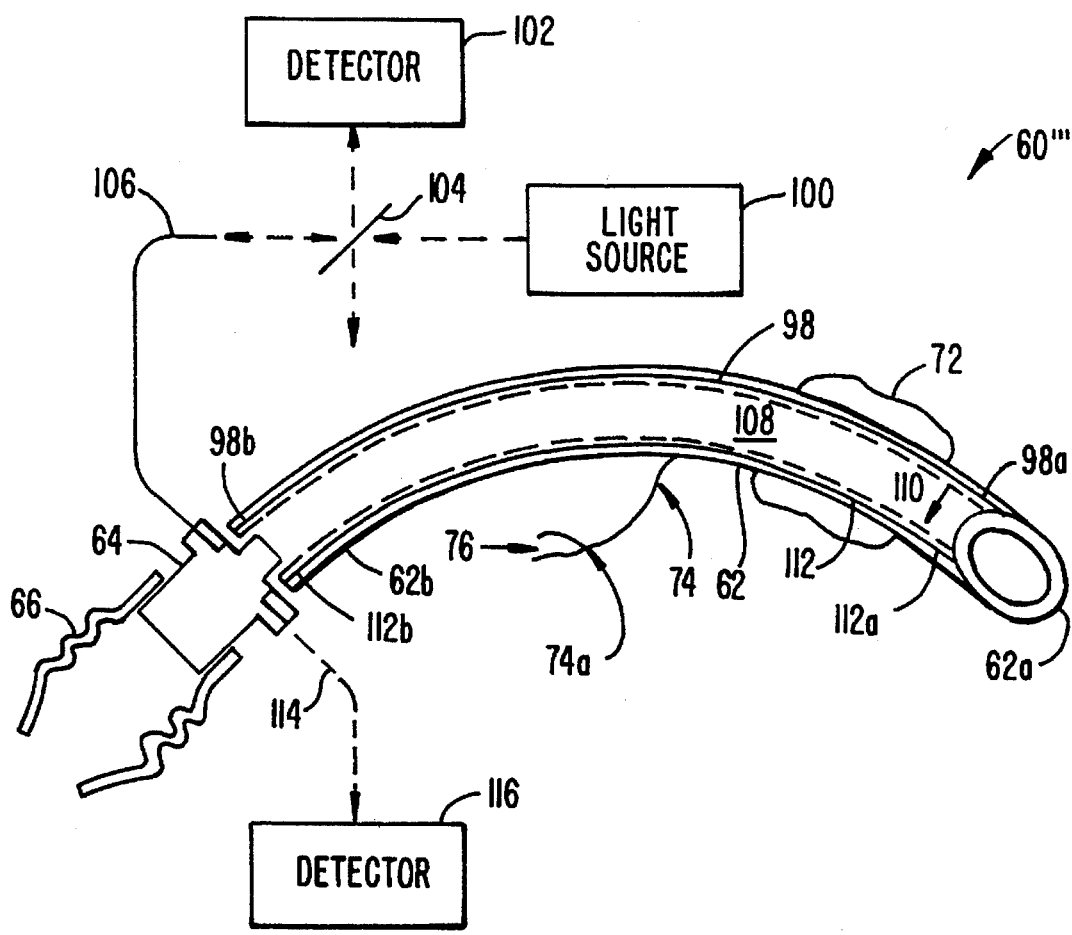
FIG. 4D is a longitudinal cross-sectional view of an endotracheal tube including an optical path to illustrate a further embodiment of the present invention.

FIG. 4D is a longitudinal cross-sectional view of endotracheal tube 62 including an optical path 98 to illustrate a further embodiment of the present invention. In this embodiment, a conventional endotracheal tube may be modified to incorporate one or more optical paths. In this manner, endotracheal system 60 may be structured to provide both optical path 78 of FIG. 4B for temperature sensing and optical path 98 of FIG. 4D for respiratory gas sensing.

As shown in FIG. 4D, the wall or lumen of tube 62 includes an optical path 98 with a first end 98a and a second end 98b. End 98b is connected to a light source 100, optionally to a detector 102 through a beam splitter 104, and to optical path 106, where path 106 is optically connected to end 98b at one end through connector 64 and to light source 100 either directly or indirectly through optional beam splitter 104 at the other end. Although the presence and use of detector 102 and beam splitter 104 are optional in the present invention, detector 102 may be used to determine oxygen saturation in the blood of a subject's tracheal tissue, as described in the present inventor's U.S. Pat. No. 5,193,544.

Preferably, system 60'" of FIG. 4D is used to monitor the end-tidal carbon dioxide concentration. The respired gases from the trachea of the subject pass through chamber or lumen 108 inside tube 62 before the gases escape through connector 64 and tube 66 to the respirator. Light emitted from end 98a of optical path 98 passes through the medium in chamber 108 along direction 110 and is collected by end 112a of a second optical path 112 also provided in the wall or lumen of tube 62. Conveniently, end 112a may be located on the opposite side of tube 62 from end 98a. The light so received passes to the other end 112b of second optical path 112 and is connected by yet another optical path 114 to a second detector 116. By comparing the intensity of light at appropriate frequencies detected by detector 116 to the light provided by light source 100, the concentration of the carbon dioxide in chamber 108 along path 110 may be determined. In such manner, both carbon dioxide concentration and other gas concentrations in the respired gases of the subject, including the end-tidal carbon dioxide concentration, may be determined.

Aspects of the embodiment of FIG. 4D are fully described in U.S. Pat. No. 5,193,544 to Richard A. Jaffe which issued on Mar. 16, 1993 from application Ser. No. 650,824 which was filed on Jan. 31, 1991, the entire disclosure of which is incorporated herein by reference.

According to the present invention, a method for measuring core body temperature of a subject comprises sensing a temperature-related parameter of the subject and generating a first signal representative of the temperature-related parameter; sensing a respiration-related parameter of respired gases of the subject and generating a second signal representative of the respiration-related parameter; and determining from the second signal an optimal time interval for measurement of a core body temperature of the subject and obtaining from the first signal a value for the core body temperature during said optimal time interval. According to an aspect of this temperature measuring method, the step of generating the first signal includes generating a first signal which is representative of a temperature of the respired gases throughout at least one respiratory cycle. Similarly, according to another aspect, the step of generating the second signal includes generating a second signal which is representative of a respiration of the respired gases throughout at least one respiratory cycle.

According to a further aspect, generating the first signal includes generating a first signal which represents a temperature of the respired gases from inspiration through expiration and generating the second signal includes generating a second signal which represents a respiration of respired gases from inspiration through expiration. In this method, the expiration is defined as including an end-tidal respiratory interval which terminates prior to subsequent inhalation. Thus, the step of determining the optimal time interval includes determining from the second signal an optimal time interval which corresponds to the end-tidal respiratory interval, and the step of determining the temperature-related parameter includes determining a temperature-related parameter during the end-tidal respiratory interval and relating this temperature-related parameter to the core body temperature to obtain a value for the core body temperature of the subject.

The method of the present invention may further comprise a step of calculating an average of the core body temperature value over at least one respiratory cycle. Calculating such an average generally comprises taking periodic samples of the first signal to obtain at least one value for the core body temperature of the subject over at least one respiratory cycle, and taking an average of the obtained value or values. The method may further comprise a step of displaying the core body temperature value, its average, or both.

As described in relation to the system of the present invention, both temperature sensing device 22 and respiratory gas sensing device 24 have alternative sites within the respiratory gas stream. Thus, the present method may include placing a temperature sensing and a respiratory gas sensing device in contact with the respired gases. Additionally, the method may include inserting a tube within a tracheal lumen of the subject and placing a temperature sensing device and/or a respiratory gas sensing device within the tube.

Preferably, the present method includes providing a temperature sensor and at least one optical path along the tube for passage of light signals, providing light via the optical path to transverse the temperature sensor and to be absorbed according to the temperature of the temperature sensor, sensing light reflected from the temperature sensor and generating a first signal that is representative of the reflected light, as described in relation to FIG. 4B. Additionally, the present method preferably includes providing at least one optical path along the tube for passage of light signals, providing light via the optical path to illuminate a portion of the trachea or locations within a medium in the tracheal lumen, sensing light reflected from the trachea or transmitted through the medium in the tracheal lumen, and generating a second signal that is representative of the reflected light, as described in relation to FIG. 4D.

While the invention has been described by reference to the various embodiments described above, it will be understood that various modifications may be made without departing from the scope of the invention. All such modifications are within the scope of the invention. The invention is to be limited only by the scope of the appended claims.

What is claimed is:

1. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said temperature sensing device is a temperature-sensitive dye.

2. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said temperature sensing device includes an optical path which is coupled to a sensor for sensing said temperature-related parameter.

3. The system of claim 2, wherein said optical path includes an optical fiber.

4. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameters; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said respiratory gas sensing device is adapted to sense a direction of a flow of respired gases.

5. The system of claim 4, wherein said respiratory gas sensing device includes a substantially deflectable vane that is responsive to said direction of the flow of respired gases and a force transducer connected thereto that is responsive to a deflection of said vane.

6. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said respiratory gas sensing device is an analyzer for measuring carbon dioxide concentration of gases respired by the subject.

7. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said respiratory gas sensing device includes an impedance measuring device, in electrical communication with an electrocardiogram device, for measuring thoracic impedance.

8. A system for enabling the measurement of core body temperature of a subject in vivo, comprising:

a tube suitable for insertion into a trachea of the subject and for conveying gases to and from the trachea;

a temperature sensing device for sensing a temperature-related parameter of the subject and generating a first signal representative of said temperature-related parameter, wherein said temperature sensing device includes an optical path which is coupled to a sensor for sensing said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval.

9. The system of claim 8, wherein said optical path forms part of said tube.

10. The system of claim 8, wherein said optical path includes an optical fiber.

11. The system of claim 10, wherein said optical fiber forms part of said tube.

12. A system for enabling the measurement of core body temperature of a subject in vivo, comprising:

a tube suitable for insertion into a trachea of the subject and for conveying gases to and from the trachea;

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter, said respiratory gas sensing device comprising at least one light source, at least one light detector, and at least two optical paths, a first path having an output end and transmitting light from a light source to the output end and through the output end to gases within said tube, and a second path having an input end for receiving light that has passed through said gases from the output end, the second path transmitting said received light to the detector for measuring respiratory gas concentrations in the tube; and a signal correlation device connected to said temperature and said respiratory gas sensing devices for determining from said second signal an optimal time interval for measurement of a core body temperature of the subject and obtaining from said first signal a value for said core body temperature during said optimal time interval.

13. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said temperature sensing device is a temperature-sensitive liquid crystal display.

14. A system for enabling the measurement of core body temperature of a subject in vivo, comprising:

a temperature sensing device for sensing a temperature-related parameter of the subject and generating a first signal representative of said temperature-related parameter;

a respiratory gas sensing device for sensing a respiration-related parameter of the subject and generating a second signal representative of said respiration-related parameter; and a signal correlation device connected to said temperature and said respiratory gas sensing devices for determining from said second signal an optimal time interval for measurement of a core body temperature of the subject and obtaining from said first signal a value for said core body temperature during said optimal time interval, wherein said respiratory gas sensing device is an analyzer for measuring oxygen concentration of gases respired by the subject.

15. The system of any one of claims 6 and 14, in which said analyzer is a mass spectrometer.

16. The system of any one of claims 6 and 14, which said analyzer is a Raman spectrometry gas analyzer.

17. The system of any one of claims 6 and 14, in which said analyzer is an infrared analyzer.

* * * * *